(12) United States Patent
Reeh

(10) Patent No.: US 11,288,982 B2
(45) Date of Patent: Mar. 29, 2022

(54) PORTABLE MULTIFUNCTIONAL ANATOMICAL MODEL FOR MEDICAL TRAINING

(71) Applicant: Chad Douglas Reeh, Okotoks (CA)

(72) Inventor: Chad Douglas Reeh, Okotoks (CA)

( * ) Notice: Subject to any disclaimer, the term of this patent is extended or adjusted under 35 U.S.C. 154(b) by 171 days.

(21) Appl. No.: 16/574,520

(22) Filed: Sep. 18, 2019

(65) Prior Publication Data

US 2020/0090550 A1 Mar. 19, 2020

Related U.S. Application Data

(60) Provisional application No. 62/732,700, filed on Sep. 18, 2018.

(51) Int. Cl.
| | | |
|---|---|---|
| *G09B 23/30* | (2006.01) | |
| *G09B 23/34* | (2006.01) | |
| *G09B 23/32* | (2006.01) | |
| *A61F 5/01* | (2006.01) | |

(52) U.S. Cl.
CPC ............ *G09B 23/303* (2013.01); *G09B 23/32* (2013.01); *G09B 23/34* (2013.01); *A61F 5/01* (2013.01)

(58) Field of Classification Search
CPC ......... G09B 23/28; G09B 23/30; G09B 23/32
USPC .................................. 434/262, 267, 272, 273
See application file for complete search history.

(56) References Cited

U.S. PATENT DOCUMENTS

| | | | | |
|---|---|---|---|---|
| 5,472,345 A * | 12/1995 | Eggert | ................. | G09B 23/281 434/273 |
| 7,544,062 B1 * | 6/2009 | Hauschild | ............ | G09B 23/285 434/267 |
| 7,553,159 B1 * | 6/2009 | Amal | .................... | G09B 23/281 434/267 |
| 7,748,984 B2 * | 7/2010 | McAllister | ............. | G09B 23/30 434/274 |
| 8,944,825 B2 * | 2/2015 | Reid-Searl | ............. | G09B 23/30 434/267 |
| 9,240,130 B2 * | 1/2016 | Carvajal | ............... | G09B 23/303 |
| 9,318,032 B2 * | 4/2016 | Samosky | ............. | G09B 23/285 |
| 9,373,270 B2 * | 6/2016 | Miyazaki | ............. | G09B 23/303 |
| 9,472,123 B2 * | 10/2016 | Trotta | .................... | B29C 39/123 |
| 10,242,598 B2 * | 3/2019 | Ozaki | ..................... | G09B 23/34 |
| 10,347,156 B2 * | 7/2019 | Robertson | .............. | G09B 23/30 |
| 10,706,744 B2 * | 7/2020 | Taylor | ........................ | A61F 2/26 |
| 2010/0196865 A1 * | 8/2010 | Kays | ...................... | G09B 23/32 434/268 |
| 2013/0052626 A1 * | 2/2013 | Hoskins | ............... | G09B 23/285 434/268 |
| 2014/0011172 A1 * | 1/2014 | Lowe | ................... | G09B 23/281 434/273 |
| 2017/0287364 A1 * | 10/2017 | Price | ...................... | G09B 23/32 |

(Continued)

*Primary Examiner* — Kurt Fernstrom
(74) *Attorney, Agent, or Firm* — Parlee McLaws LLP; Kirsten M. Oates

(57) ABSTRACT

A multifunctional anatomical model for training includes a hand portion coupled to a forearm portion; the forearm portion coupled to a base portion; and the base portion coupled to a female external genitalia portion and a male external genitalia portion. The model is movable into a plurality of stable positions. Each position allows access to one or more features simulating one or more clinical skills and disposed on the hand portion, the forearm portion, the female external genitalia portion, and the male external genitalia portion.

20 Claims, 7 Drawing Sheets

(56) References Cited

U.S. PATENT DOCUMENTS

2018/0330637 A1* 11/2018 Jarratt .................... G09B 23/34
2020/0126449 A1* 4/2020 Horst ................... G09B 23/286

* cited by examiner

PORTABLE MULTIFUNCTIONAL ANATOMICAL MODEL FOR MEDICAL TRAINING

CROSS REFERENCE TO RELATED APPLICATION

This application claims benefit and priority to U.S. Provisional Application No. 62/732,700 filed Sep. 18, 2018, the disclosure of which is incorporated by reference herein in its entirety.

FIELD OF THE INVENTION

The present invention is directed to a portable multifunctional anatomical model for medical training.

BACKGROUND OF THE INVENTION

Medical simulation has become especially useful in medical education with an increased focus on building competency in clinical skills and diagnostic procedures. Simulation training using anatomical models rather than live subjects or cadavers has proven effective to link theoretical nursing or medical student training and clinical experience, and is used to demonstrate, practice, and assess clinical skills.

For such purpose, anatomical models are currently available for many basic organs, functions, and clinical skills including, but not limited to, anatomy pathology models; nervous system models; skin models; vertebrae models; human spine models; hand and foot models; ear, nose, and throat models; breast models; joint models; acupuncture models; brain models; digestive models; genital and pelvis models; heart and circulatory models; human muscle models; skeleton models; urology models; and the like. Typically, an anatomical model is specific for a single organ, function, or clinical skill. However, full-size anatomical mannequins incorporating multiple basic organs and functions to practice numerous clinical skills have been developed.

However, when teaching nursing or medical students, the need to purchase numerous separate models or full-size anatomical mannequins for teaching or demonstration purposes can be exorbitantly expensive for universities and teaching hospitals. Further, storage space or room for multiple models may be limited in the classroom. Students are typically provided access to the models only in the classroom, and are usually restricted from removing such expensive models for home study, requiring students to spend extra time in the classroom after hours in order to practice their clinical skills. Anatomical models tend to be bulky, heavy, and difficult to transport or handle due to having many loose or easily removable components. Purchasing anatomical models for personal study or practice at home may far exceed the student's budget.

Accordingly, there is a need in the art for an improved inexpensive anatomical model for medical training, particularly for nursing and medical students who would prefer to study or practice at home.

SUMMARY OF THE INVENTION

The present invention relates to a portable multifunctional anatomical model for medical training. In one aspect, the invention comprises a multifunctional anatomical model for training comprising:

a hand portion coupled to a forearm portion;
the forearm portion coupled to a base portion; and
the base portion coupled to a female external genitalia portion and a male external genitalia portion;
wherein the model is movable into a plurality of stable positions, each position allowing access to one or more features simulating one or more clinical skills and disposed on the hand portion, the forearm portion, the female external genitalia portion, and the male external genitalia portion.

In one embodiment, the hand portion, the forearm portion, the base portion, the female external genitalia portion, and the male external genitalia portion define a unitary hollow cavity extending therethrough to allow passage of liquid or removable insertion of one or more liquid cartridges proximal to or at the site of the one or more features. In one embodiment, the fingertips of the hand define one or more apertures to drain the liquid externally from the cavity.

In one embodiment, the base is frustoconical comprising a circular face, a curved surface, and an edge, and defines an upturned lip disposed on the edge. In one embodiment, the base portion is removably attached to the forearm portion.

In one embodiment, the stable positions are selected from palm upward, index finger and thumb upward, palm downward, or little finger upward.

In one embodiment, the position comprises palm upward. In this position, in one embodiment, the hand portion enables simulation of glucose monitoring or splinting. Further, in one embodiment, the forearm defines a plurality of veins enabling simulation of intravenous insertion and phlebotomy, the veins being selected from a cephalic vein, a median cubital vein, a basilic vein, a pronator vein, a median antebrachial vein, a brachial vein, and paired ulnar veins.

In one embodiment, the position comprises index finger and thumb upward. In this position, in one embodiment, the hand portion defines a burn wound enabling simulation of burn management. Further, in one embodiment, the forearm portion supports a tracheostomy enabling simulation of cleaning and suctioning.

In one embodiment, the position comprises palm downward. In this position, in one embodiment, the hand portion defines a plurality of veins enabling simulation of intravenous insertion, the veins being selected from a cephalic vein or a dorsal venous network. In one embodiment, the model further comprises a wrist portion enabling simulation of casting or splinting. In one embodiment, the forearm portion defines a simple wound and one or more closing means selected from a staple, suture, skin closure tape, adhesive, or adhesive skin closures (for example, a 3M™ Steri-strip™), to enable simulation of wound management. Further, in one embodiment, the forearm portion defines a complex wound enabling simulation of wound management. Further, in one embodiment, the forearm supports one or more draining means selected from a Penrose drain, a Hemovac drain, a Jackson-Pratt drain, or a chest tube drain, to enable simulation of drain management.

In one embodiment, the position comprises little finger upward. In this position, in one embodiment, the model further comprises a nose portion simulating nasogastric intubation in a High Fowler's position. Further, in one embodiment, the forearm portion supports an ostomy simulating cleaning and removal or attachment of an ostomy pouching system.

In one embodiment, the female external genitalia portion and the male external genitalia portion are configured to simulate urinary catheterization.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described by way of an exemplary embodiment with reference to the accompanying simplified, diagrammatic, not-to-scale drawings. In the drawings.

DETAILED DESCRIPTION OF PREFERRED EMBODIMENTS

Figure 1:
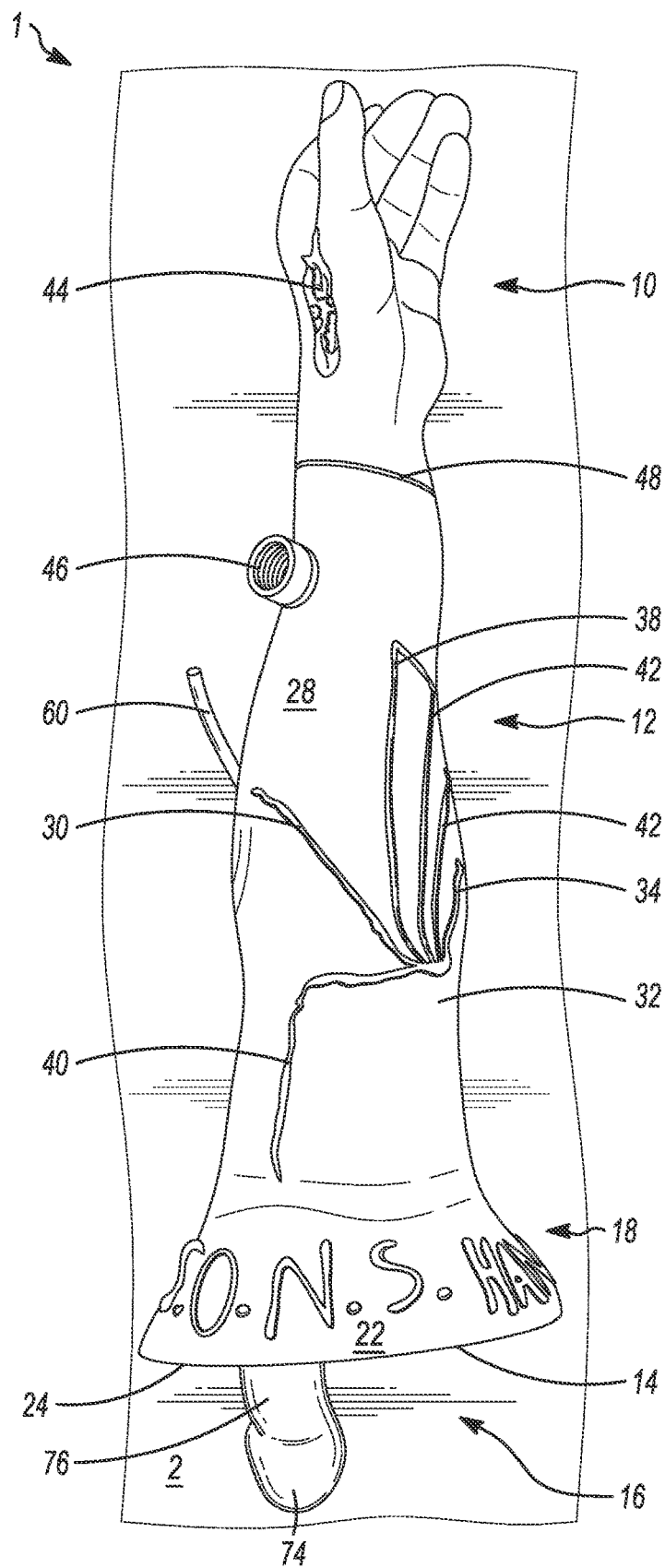
FIG. 1 is a front view of one embodiment of the present invention, with the left arm positioned with the palm of the hand facing upwardly, the hand being at rest or in the position of function.

Before the present invention is described in further detail, it is to be understood that the invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a," "an," and "the" include plural referents unless the context clearly dictates otherwise.

The present invention comprises a portable multifunctional anatomical model for medical training of healthcare professionals, particularly nursing and medical students, and well-trained patients participating in their homecare. The invention enables students to demonstrate, practice, and assess multiple clinical skills on a single, realistic anatomical model. Further, the anatomical model is lightweight, portable, and inexpensive, thereby enabling students to transport the model to and from the classroom or home for personal study or extra practice in clinical skills. Preferably, the anatomical model is for use in helping assisting nursing students on necessary skills (also termed as "H.A.N.S.O.N.S. Hand").

The invention will now be described having reference to the accompanying Figures. The anatomical model (1) is shown generally in the Figures to comprise replicas of multiple anatomical structures of a human, and features enabling training or demonstration of clinical skills. In one embodiment shown in FIGS. 1-7, the anatomical model (1) comprises a hand portion (10), a forearm portion (12), a female external genitalia portion (14), and a male external genitalia portion (16). In one embodiment, the anatomical model (1) further comprises a nose portion (not shown).

As shown in FIGS. 1-4 and 6-7, the anatomical model (1) comprises in sequence, from top to bottom, the hand portion (10) coupled to the forearm portion (12). The forearm portion (12) is coupled to the base portion (18). The female external genitalia portion (14) and the male external genitalia portion (16) are coupled to the base portion (18). While the anatomical model (1) shown in FIGS. 1-4 and 6-7 simulates a left hand and left forearm, it will be appreciated by those skilled in the art that a right hand and right forearm may also be suitable for the present invention.

In one embodiment, the anatomical model (1) is hollow. The hand portion (10), forearm portion (12), base portion (18), female external genitalia portion (14), and male external genitalia portion (16) may be configured as one piece or as separate pieces which are interconnected to together define a unitary hollow cavity (not shown) extending therethrough. The cavity may be used to receive any liquid (for example, saline, water, or other liquid) which may be injected into a specific feature of the anatomical model (1) during training in a clinical skill. The cavity may be also used to attach therein one or more cartridges comprising liquid (for example, colored liquid mimicking blood) which are positioned proximal to or at the site of a particular feature (for example, a vein) such that the liquid is expelled from the cartridge, thereby providing direct feedback to the student or trainee about his performance. The feedback is then used in following training sessions to correct and improve the clinical techniques.

In one embodiment, one or more fingertips of the hand portion (10) define one or more apertures (not shown) through which any liquid within the cavity may be drained externally. In one embodiment, the anatomical model (1) may be configured with a base portion (18) which is removably attached to the forearm portion (12) (for example, using threads, tabs, snap-fit, and the like) in order to allow insertion, removal, or replacement of cartridges within the cavity.

In one embodiment, the hand portion (10) is provided in the position of function. As used herein, the term "position of function" refers to the hand portion (10) being at a rest or neutral position including 20-30 degrees of wrist extension, 45 degrees of metacarpal joint flexion, 30 degrees of proximal interphalangeal joint flexion, and 20 degrees of distal interphalangeal joint flexion.

However, it will be appreciated by those skilled in the art that the hand portion (10) may be provided in a fist position which is also suitable for the present invention. As used herein, the term "fist position" refers to the hand being clenched with the fingers doubled into the palm and the thumb doubled inward across the fingers.

In one embodiment, the base portion (18) is substantially frustoconical in shape. As used herein, the term "frustoconical" means having the shape of a cone with the vertex removed parallel to a circular face (20), a curved surface (22), and an edge (24). In one embodiment, the base portion (18) defines an upturned lip (26) disposed on the edge (24).

The anatomical model (1) is movable into a plurality of stable positions, each position allowing access to one or more features simulating one or more clinical skills and disposed on the hand portion, the forearm portion, the female external genitalia portion, and the male external genitalia portion, as will be further described.

The hand portion (10) and the base portion (18) together allow the anatomical model (1) to rest stably in a substantially horizontal position on any underlying support surface (2) (for example, a table, desk, countertop, etc.) while being used for training. As used herein, the term "horizontal" means the orientation of a plane or line that is substantially parallel to the plane of the horizon. In the horizontal position shown in FIGS. 1-5, the hand portion (10) in either the position of function or fist position, and the edge (24) of the base portion (18) rest on the underlying support surface (2).

Figure 2:
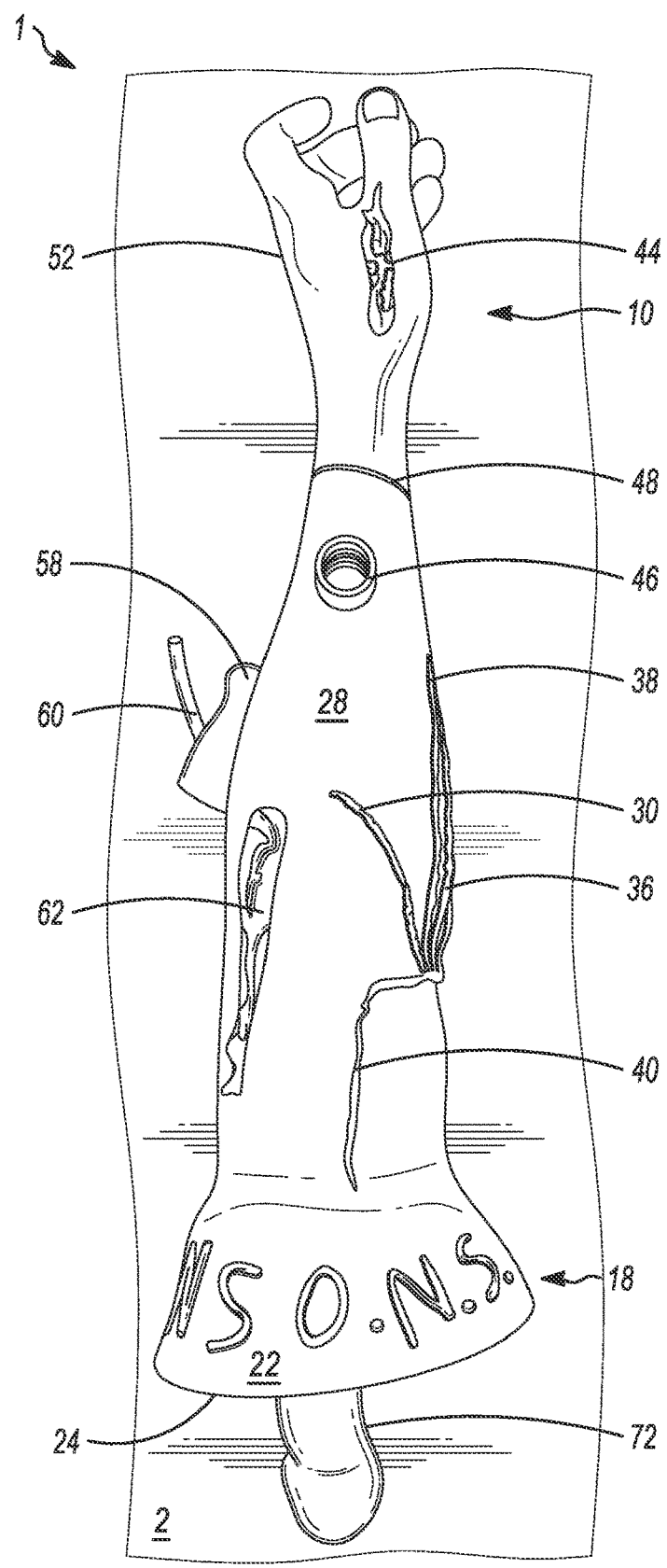
FIG. 2 is a side view of the embodiment shown in FIG. 1, with the left arm positioned with the index finger and thumb of the hand facing upwardly.
Figure 6:
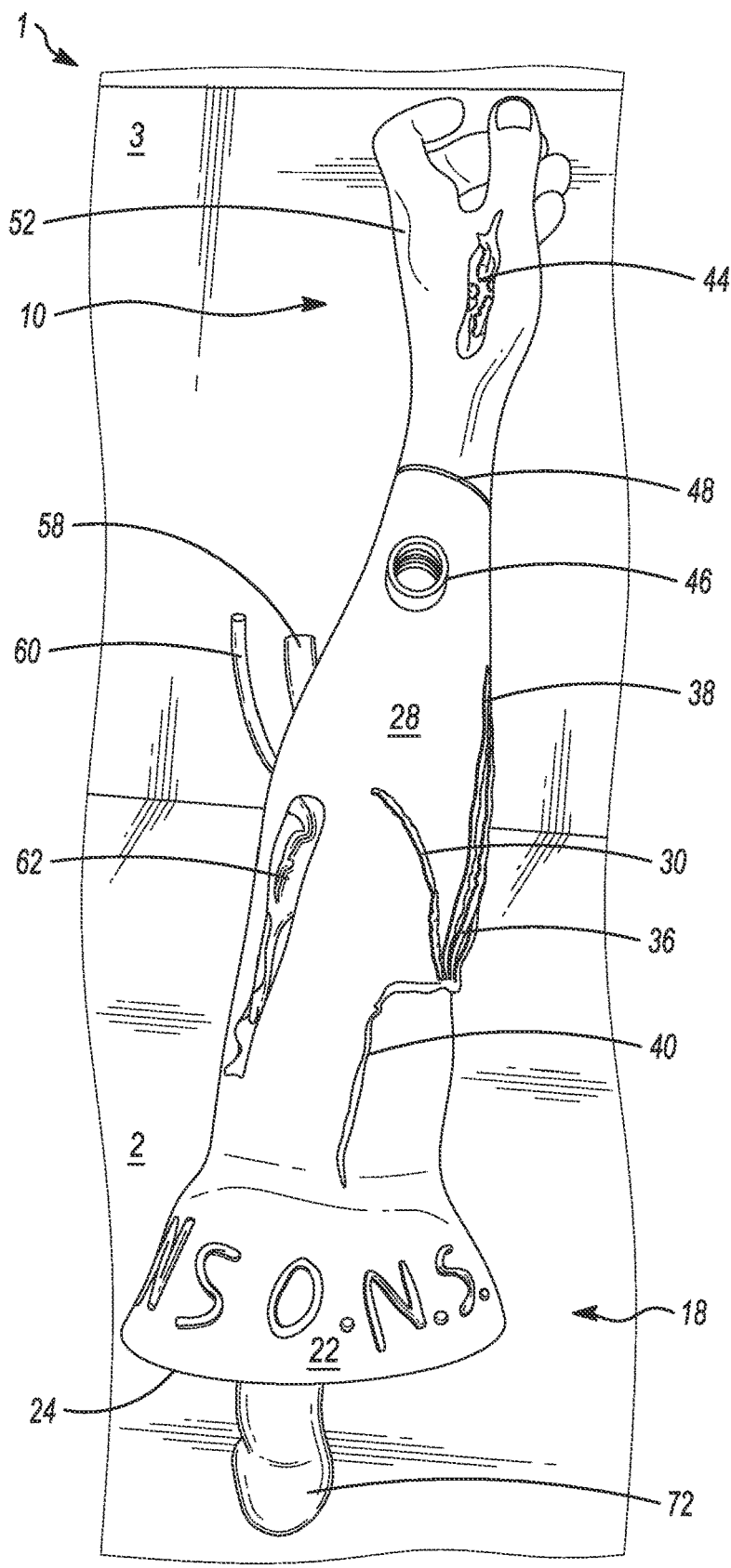
FIG. 6 is a side view of the embodiment shown in FIG. 1, with the left arm positioned with the index finger and thumb of the hand facing upwardly, and the anatomical model resting stably in the vertical position.
Figure 7:
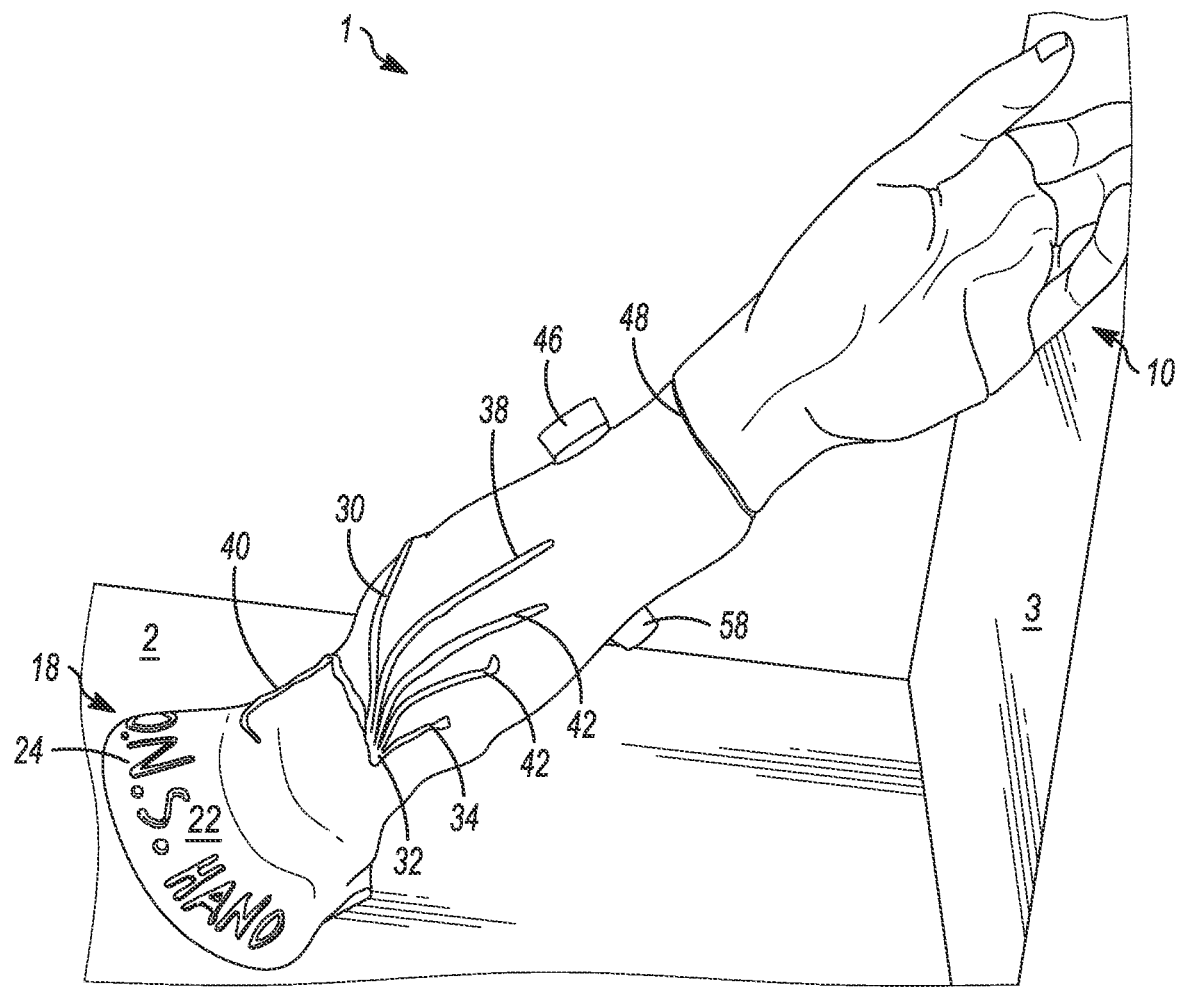
FIG. 7 is a front view of one embodiment of the present invention, with the left arm positioned with the palm of the hand facing upwardly, the hand being at rest or in the position of function, and the anatomical model resting stably in the vertical position.

The anatomical model (1) can also rest stably in the vertical position. As used herein, the term "vertical" means the orientation of a plane or line that is substantially at a right angle to the horizontal plane. As shown in FIGS. 2 and 6-7, the lip (26) of the base portion (18) may rest on the underlying support surface (2) with the hand portion (10) against a vertical support surface (3), thereby orienting or tilting the hand portion (10) upwardly at an angle relative to the underlying support surface (2) or at an angle to the vertical support surface (3).

Figure 3:
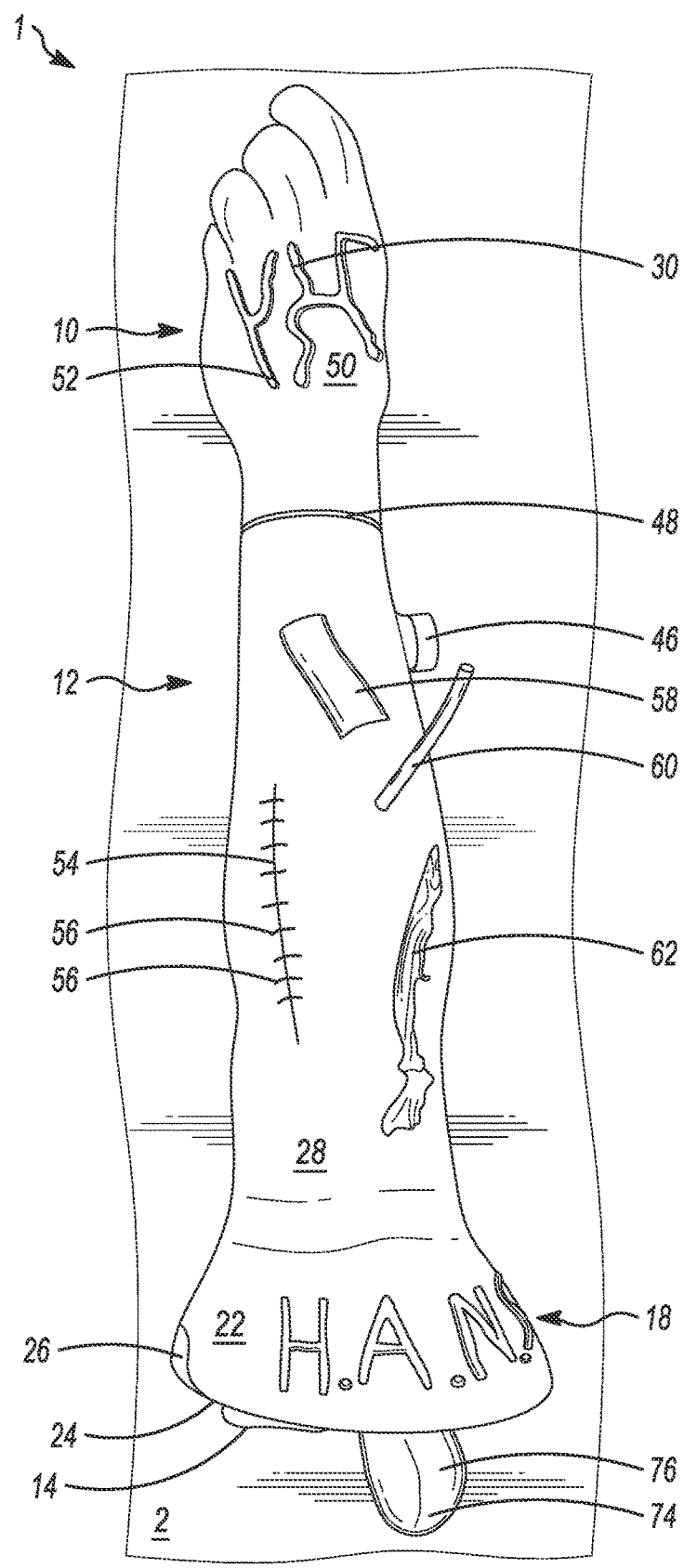
FIG. 3 is a back view of the embodiment shown in FIG. 1, with the left arm positioned with the palm of the hand facing downwardly.
Figure 4:
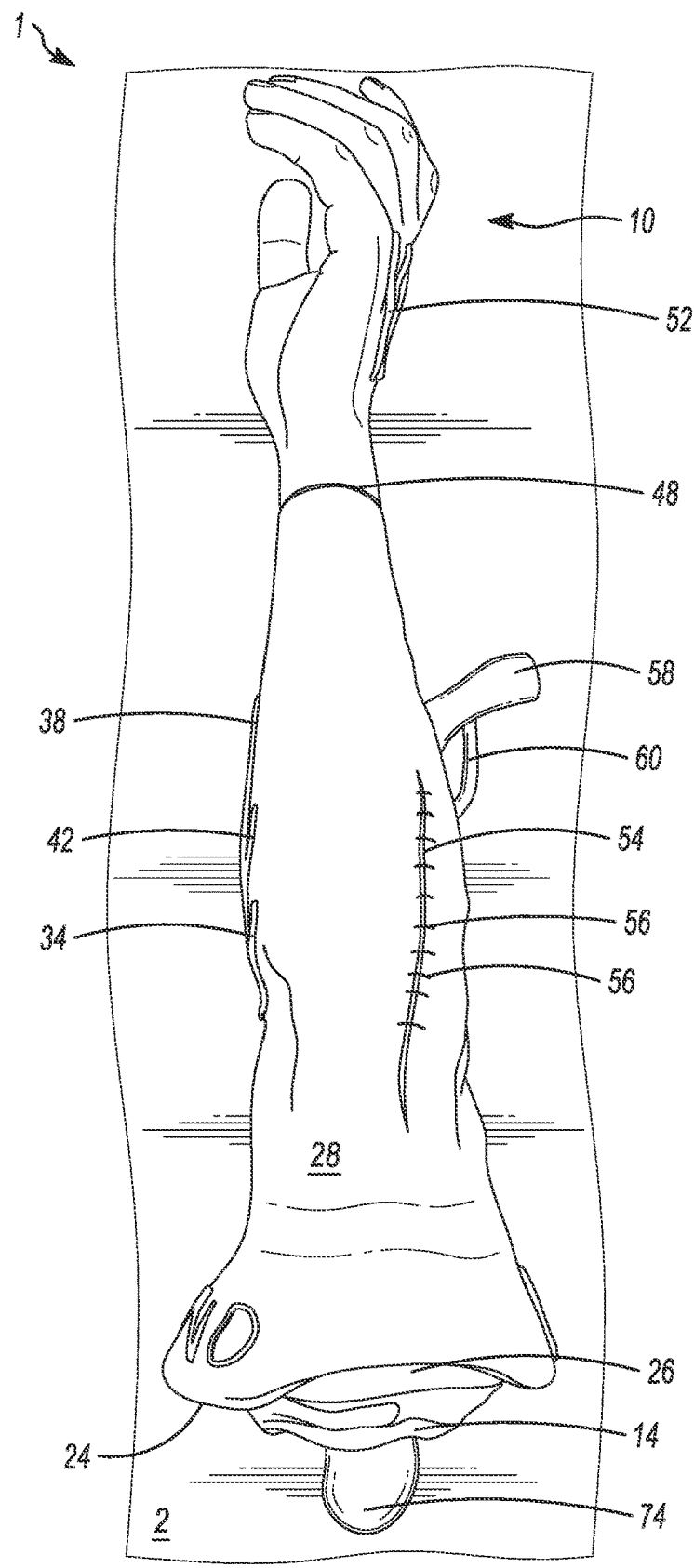
FIG. 4 is a side view of the embodiment shown in FIG. 1, with the left arm positioned with the little finger of the hand facing upwardly.

The anatomical model (1) may rest stably in four hand positions including palm facing upwardly (FIG. 1); the index finger and thumb facing upwardly (FIG. 2); palm of the hand facing downwardly (FIG. 3); and little finger facing upwardly (FIG. 4). In each of the four hand positions, the anatomical model (1) provides multiple training features simulating one or more clinical skills and disposed on the hand portion, the forearm portion, the female external genitalia portion, and the male external genitalia portion.

As shown in FIG. 1, the "palm upward" position provides access to the thumb and fingers of the hand portion (10). In one embodiment, any finger may be used to practice a finger-prick test by which the finger is pricked with a lancet to obtain a drop of blood for blood glucose monitoring or diabetes testing. In one embodiment, the hand portion (10) may be used to practice applying various types of finger splints for treating thumb or finger injuries including, but not limited to, buddy splints, static splints, metal or foam static splints, stack splints, and dynamic splints.

The forearm portion (12) extends between the hand portion (10) and the base portion (18), and defines replicas of multiple veins positioned anatomically correctly on its surface (28) for practicing intravenous insertion and phlebotomy. As used herein, the term "intravenous insertion" refers to a procedure whereby a vein is punctured through the skin by a cannula to provide venous access for administration of fluids, medications, chemotherapy, blood products, etc. In one embodiment, the veins provided on the surface (28) of the forearm portion (12) for practicing intravenous insertion include, but are not limited to, the cephalic vein (30), median cubital vein (32), basilic vein (34), pronator vein (36), median antebrachial vein (38), brachial vein (40), and paired ulnar veins (42).

As used herein, the term "phlebotomy" refers to the drawing of blood by venipuncture for diagnostic testing, transfusion, apheresis, and experimental procedures. In one embodiment, the veins include, but are not limited to, the median cubital vein (32).

In one embodiment, one or more cartridges (not shown) of colored fluid (for example, red colored fluid mimicking blood) are positioned within the cavity of the anatomical model (1) proximate to or in the area of each vein (30, 32, 34, 36, 38, 40, 42). Venipuncture of any vein (30, 32, 34, 36, 38, 40, 42) causes release of the colored fluid from the cartridge, thereby simulating release of "blood" and indicating to the student or trainee that intravenous insertion or phlebotomy has been successfully performed.

As shown in FIG. 2, the index finger and thumb of the hand portion (10) face upwardly. In one embodiment, a burn wound (44) is defined on the hand portion (10), and is positioned below the index finger and thumb in the area of the flexor pollicis brevis muscle. Management of the burn wound (44) may be practiced including, but not limited to, calculation of the total body surface area of the burn wound (44), burn depth assessment, and cleansing and dressing of the burn wound (44).

Also shown in FIG. 2, the lip (26) of the base (18) may rest on the underlying support surface (2) so that the anatomical model (1) is placed in the horizontal position. As shown in FIGS. 6 and 7, the lip (26) of the base (18) may rest on the underlying support surface (2) with the hand portion (10) resting against a vertical support surface (3) so that the anatomical model (1) is placed in the vertical position, thereby orienting or tilting the hand (10) upwardly at an angle relative to the underlying support surface (2). In the vertical position, the anatomical model (1) may mimic a patient being placed in a High Fowler's position. As used herein, the term "High Fowler's position" refers to a position in which the patient is seated in a semi-upright sitting position (60-90 degrees) and may have the knees bent or straight. This position is commonly used in a patient having a tracheostomy (46).

In one embodiment, the forearm portion (12) supports a tracheostomy (46) on its surface (28). As used herein, the term "tracheostomy" refers to an opening surgically created through the neck into the trachea to allow placement of a tracheostomy tube, thereby providing an artificial airway for a patient requiring long term airway support. In one embodiment, the tracheostomy (46) is positioned proximal to and below a wrist portion (48). The tracheostomy (46) comprises an inner cannula and an outer cannula to facilitate practice of cleaning of the stoma and suctioning of the tracheostomy tube for managing respiratory secretions in a patient. In one embodiment, one or more cartridges (not shown) containing fluid mimicking respiratory secretions are positioned within the cavity of the anatomical model (1) in the area beneath the tracheostomy (46). Suctioning causes uptake of the fluid from within the cartridge, thereby simulating effective suctioning of "respiratory secretions."

The student or trainee can practice tracheostomy-related techniques including, but not limited to, cleaning of the stoma; application of Steristrips™, gauze, and dressing; and suctioning by inserting a suction catheter through the inner cannula, advancing the suction catheter to the correct depth within the inner cannula while keeping the suction port open, and suctioning the airway in a circular motion as the suction catheter is removed while the suction port is closed.

In one embodiment, the forearm portion (12) supports an ostomy or stoma (not shown). As used herein, the term "ostomy" refers to a surgically created opening from an area inside the body to the outside to allow stool or urine to pass either from the intestine or urinary tract respectively. The stoma may be positioned proximal to the tracheostomy (46) in order to practice care of the ostomy (for example, cleaning around the stoma) and ostomy pouching system (for example, removal of the used pouching system and attachment of a new pouching system).

As shown in FIG. 3, the "palm downward" position provides access to the back surface (50) of the hand portion (10) which defines replicas of multiple veins for practicing intravenous insertion. In one embodiment, the veins provided on the back surface (50) of the hand portion (10) for practicing intravenous insertion include, but are not limited to, the cephalic vein (30) and the dorsal venous network (52).

In one embodiment, one or more cartridges (not shown) of colored fluid (for example, red colored fluid mimicking blood) are positioned within the cavity of the anatomical model (1) proximate to or in the area of the veins (30, 52). Venipuncture of any vein (30, 52) causes release of the colored fluid from the capsule, thereby simulating release of "blood" and indicating to the student or trainee that intravenous insertion has been successfully performed.

In one embodiment, a wrist portion (48) positioned between the hand portion (10) and forearm portion (12) has been "fractured" to practice placement of a plaster cast or splint. Skills which may be practiced using the fractured wrist portion (48) include, but are not limited to, applying cloth, padding, or an elastic bandage in preparation for application of the casting material; applying the casting material; and removing the cast.

In one embodiment, the forearm portion (12) defines a replica of a simple wound (54) "closed" by a plurality of staples (56). As used herein, the term "simple wound" refers to a superficial wound which has affected only the epidermis. In one embodiment, the simple wound (54) extends along the length of the forearm portion (12) to allow application of a dressing overtop the staples (56) employing aseptic non-touch technique. In one embodiment, the simple wound (54) and staples (56) are positioned on the left side of the forearm portion (12). Wound management skills which may be practiced using the simple wound (54) and staples (56) include, but are not limited to, cleaning the outer edges of the simple wound (54), swabbing the simple wound (54), applying the appropriate dressing, and removal of the staples (56).

It will be appreciated by those skilled in the art that other methods for closing the simple wound (54) including, but are not limited to, sutures, stitches, skin closure tape, adhesive, and adhesive skin closures (for example, a 3M™ Steri-strip™) may replace the staples (56) for holding together the edges of the simple wound (54). Techniques to apply these other methods may also be practiced on the simple wound (54) (for example, suture placement, knot tying, removal, etc.).

In one embodiment, the forearm portion (12) supports a Penrose drain (58). In one embodiment, the drain (58) is positioned proximate to and below the wrist portion (48). As used herein, the term "Penrose drain" refers to a soft pliable latex or silicone tube used as a surgical drain to promote drainage from an open wound by releasing fluids from out of the wound to outside the body. A safety pin or tab is present at the end of the drain (58) to prevent it from slipping into the wound. Skills which may be practiced using the drain (58) include, but are not limited to, applying and changing a dressing around the drain (58); pulling the tube and cutting it shorter as would be performed as the wound heals; and anchoring the tube after cutting using the safety pin.

In one embodiment, the forearm portion (12) supports a drainage tube (60) acting as a Hemovac drain, Jackson-Pratt drain, chest tube drain, or any other type of drain to remove fluids after surgery. In one embodiment, the drainage tube (60) is positioned proximate to and below the Penrose drain (58). Skills which may be practiced using the drainage tube (60) include, but are not limited to, suturing the drainage tube (60) to the skin to prevent removal; and applying and changing a dressing around the drainage tube (60).

In one embodiment, the forearm portion (12) supports a complex wound (62) comprising a concavity to practice cleaning and packing of the complex wound (62) with gauze or dressing pieces level with the skin. As used herein, the term "complex wound" refers to a wound whose healing is not progressing normally or which requires advanced care such as, for example, a stage 3, stage 4, or non-stageable pressure ulcer. In one embodiment, the complex wound (62) is positioned proximate to and below the drainage tube (60), and extends along the length of the forearm portion (12).

As shown in FIG. 4, the "upward little finger" position shows the lip (26) of the base portion (18) which may be used to rest against a vertical surface to mimic a patient being placed in the High Fowler's position as previously described. In one embodiment, the forearm portion (12) provides access to a nose (not shown) to practice insertion of a nasogastric tube required in nasogastric intubation which is performed when the patient is placed in the High Fowler's position to access the stomach to administer nutrition and medication or to remove contents from the stomach.

In one embodiment, one or more cartridges (not shown) of liquid are positioned within the cavity of the anatomical model (1) proximate to or in the area of the nose. Insertion of the nasogastric tube correctly causes release of the fluid from the capsule, thereby simulating release of "gastric juice" and indicating to the student or trainee that nasogastric intubation has been successfully performed.

In one embodiment, the forearm portion (12) supports an ostomy or stoma (not shown) as previously described. The stoma may be positioned below the nose in order to practice care of the ostomy (for example, cleaning around the stoma) and ostomy pouching system (for example, removal of the used pouching system and attachment of a new pouching system).

Figure 5:
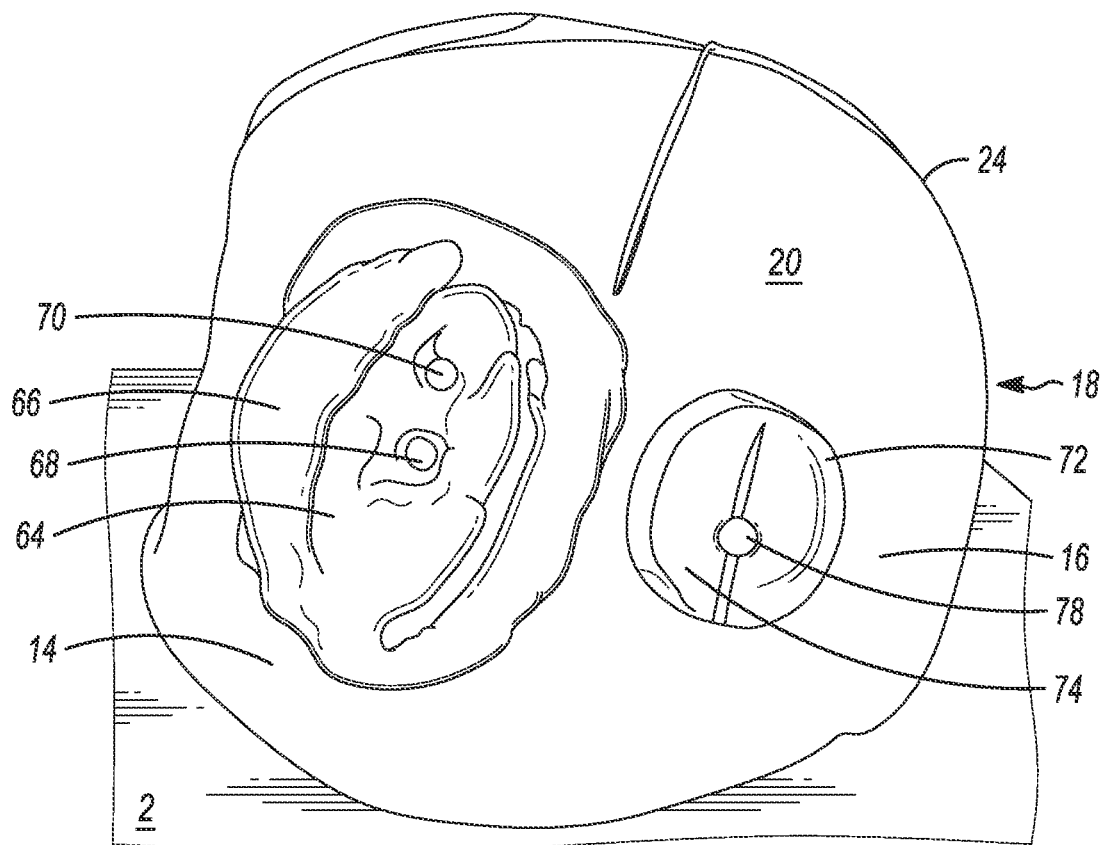
FIG. 5 is a bottom view of the embodiment shown in FIG. 1, showing the female and male external genitalia disposed on the base portion.

As shown in FIG. 5, the base portion (18) supports the female external genitalia portion (14) and the male external genitalia portion (16). In one embodiment, the female external genitalia portion (14) comprises the labium minus and labium majus (64, 66), vagina (68), and urethra (70). In one embodiment, the male external genitalia portion (16) comprises the penis (72) including the glans (74), shaft (76), and urethra (78). In one embodiment, one or more cartridges (not shown) containing liquid to replicate a bladder containing urine, is attached to the cavity of the anatomical model (1)

in the area of the female external genitalia portion (14) and male external genitalia portion (16). In one embodiment, the urethra (70, 78) allows practice of urinary catheterization using for example, intermittent catheters and Foley catheters, which typically are flexible tubes passed through the urethra (70, 78) and into the bladder to drain urine. Use of the intermittent catheter requires practice of its insertion into the bladder. Use of the Foley catheter is more technical, requiring practice in its passage through the urethra (70, 78) into the bladder, and inflation of a balloon with sterile water using a syringe when it lies inside the bladder to hold the catheter in place. Successful catheterization through the urethra (70, 78) into the bladder may be indicated by the catheter puncturing the cartridge to release the liquid contained therein. Deflation of the balloon and removal of the Foley catheter may also be practiced.

The anatomical model (1) may be formed by processes known in the art. The anatomical model (1) can be constructed from any material or combination of materials having suitable properties such as, for example, ease of manufacture, inexpensive, lightweight, durable, and appropriateness for use with any fluid to be dispensed into the cavity of the anatomical model (1).

The anatomical model (1) may be formed of appropriate materials known to those skilled in the art to ensure that the anatomical model (1) is as lightweight and portable as possible to be compact for storing in a nap sack and for easy carrying to and from class or home by a nursing student or trainee. In one embodiment, the anatomical model (1) weighs between about 1.0 pound to about 2.5 pounds.

In one embodiment, the anatomical model (1) may be formed of silicone foam (for example, Soma Foama™), silicone rubber or elastomer (for example, EcoFlex™ to mold the arm; Skin Tite™ to create wounds; Dragon Skin™ to mimic human skin), or other appropriate materials known to those skilled in the art. Preferably, materials are used which will yield an anatomical model (1) having a flexible or textured "skin" which closely resembles the color, texture, and elasticity of human skin.

The dimensions of the anatomical model (1) are not essential to the invention and are dictated by the various sizes, dimensions, and shapes of the various features of the anatomical model (1). The dimensions of the anatomical model (1) may be increased or decreased as may be required to satisfy any particular design objectives; for example, the anatomical model (1) may be made available in a variety of dimensions to correspond with different arm sizes, such as, for example, children or adults, women or men. In one embodiment, the forearm portion (12) of the anatomical model (1) may have dimensions ranging from about 8 inches (for example, a pediatric anatomical model) to about 16 inches (for example, an adult anatomical model) in length. In one embodiment, the forearm portion (12) of the anatomical model (1) may have the dimensions of an average adult male forearm ranging from about 14 inches to about 18 inches in length. Preferably, the hand portion (10) with veins (30, 52), wrist portion (48), forearm portion (12) with veins (30, 32, 34, 36, 38, 40, 42), the female external genitalia portion (14), and the male external genitalia portion (16) are configured to be anatomically correct.

It will be appreciated that the anatomical model (1) of the present invention is simple but rugged in construction that it can be made at low cost. The anatomical model (1) may be easily fabricated. The anatomical model (1) may be formed as a single, integral unit combining the hand portion (10), wrist portion (48), forearm portion (12), base portion (18), female external genitalia portion (14), and male external genitalia portion (16), or as separate pieces (for example, hand portion (10) and wrist portion (48), forearm portion (12), and base portion (18)) which are joined together.

Since the anatomical model (1) is hollow, the hand portion (10), wrist portion (48), forearm portion (12), base portion (18), female external genitalia portion (14), and male external genitalia portion (16) may be formed by dipping, molding, foaming, extrusion, and other processes known in the art. Preferably, the anatomical model (1) or components thereof are formed by molding or casting. Briefly, molding involves shaping liquid material using a mold representing the final object. Casting involves pouring a liquid material into a mold to form the desired object, and then allowing it to solidify. Molding and casting are relatively simple and rapid processes for producing the anatomical model (1) or components thereof.

The various features for training and demonstration of clinical skills (for example, the staples (56), Penrose drain (58), drainage tube (60), female external genitalia portion (14) and male external genitalia portion (16), liquid cartridges) may be manufactured separately as components which are attachable to the anatomical model (1). Any apertures or openings may be made in the appropriate components using any hole-making operations known to those skilled in the art, including but not limited to drilling, reaming, tapping, boring, and the like. Features such as the veins (30, 32, 34, 36, 38, 40, 42), burn wound (44), simple wound (54), and complex wound (62) made be formed integral with the forearm portion (12). In general, the anatomical model (1) requires few components, making the anatomical model (1) amenable to rapid assembly and minimizing expense in manufacturing.

It should be apparent, however, to those skilled in the art that many more modifications besides those already described are possible without departing from the inventive concepts herein.

The inventive subject matter is not to be restricted except in the scope of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

REFERENCES

All publications mentioned herein are incorporated herein by reference (where permitted) to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Alderson, S. W. Training aid for intravenous therapy. U.S. Pat. No. 2,995,832, issued Aug. 15, 1961.

Aponte, M. Educational medical mannequin. U.S. Pat. No. 5,314,339, issued May 24, 1994.

Chase, M. C. Injection training aid. U.S. Pat. No. 3,722,108, issued Mar. 27, 1973.

Chase, M. C. Simulated human limb. U.S. Pat. No. 3,789,518, issued Feb. 5, 1974.

Chen, X. et al. Tracheotomy training human body model. Chinese Patent Application No. 201570170, published Sep. 1, 2010.

Haver, H. T. Anatomical instruction model. U.S. Pat. No. 2,689,415, issued Sep. 21, 1954.

Hoskins, I. IV training system. United States Patent Application Publication No. 2013/0052626, published Feb. 28, 2013.

Jin. L. Wearable type ostomy nursing model. Chinese Patent Application No. 204117466, published Jan. 21, 2015.

Kohnke et al. Training apparatus for the practice of puncturing blood vessels. European Patent No. 0499125, issued Apr. 29, 1998.

Lade, J. H. Arm for teaching venipuncture and intravenous therapy. U.S. Pat. No. 2,704,897, issued Mar. 29, 1955.

Liang, X. et al. Practice model for nasogastric tube intubation and tracheal incision. Chinese Patent Application No. 202662213, published Jan. 9, 2013.

Liu, X. Fistulization nursing model. Chinese Patent Application No. 2751382, published Jan. 11, 2006.

Liu, X. et al. Multifunctional urethral catheterization model. Chinese Patent Application No. 201796535, published Apr. 13, 2011.

Liu, Y. et al. Urethral catheterization model. Chinese Patent Application No. 202258073, published May 30, 2012.

Niiranen, J. V. Synthetic arm. U.S. Pat. No. 2,686,374, issued Aug. 17, 1954.

Parry, D. et al. Wearable wound simulant. United States Patent Application Publication No. 2009/0298034, published Dec. 3, 2009.

Poole, M. W. Intravenous therapy training aid. U.S. Pat. No. 2,871,584, issued Feb. 3, 1959.

Qi, F. et al. Wound hemostatic suture model. Chinese Patent Application No. 202976650, published Jun. 5, 2013.

Sakezles, C. et al. Chest tube simulation method and training device. United States Patent Application Publication No. 2017/0011655, published Jan. 12, 2017.

Spitalnik, P. L. Pressure ulcer wound care models, methods, and kits. U.S. Pat. No. 6,241,525, issued Jun. 5, 2001.

Tortola, A. Apparatus and method for laproscopic skills training. United States Patent Application Publication No. 2012/0308977, published Dec. 6, 2012.

Wise, C. D. et al. Artificial arm. U.S. Pat. No. 4,182,054, issued Jan. 8, 1980.

Yang, S. J. et al. Arm model apparatus for intravenous injection training. United States Patent Application Publication No. 2013/0078603, published Mar. 28, 2013.

What is claimed is:

1. A portable multifunctional anatomical model for training comprising:
    a hand portion coupled to a forearm portion;
    the forearm portion coupled to a base portion; and
    the base portion coupled to a female external genitalia portion and a male external genitalia portion;
    wherein the model is movable into a plurality of stable positions, each stable position allowing access to one or more features simulating one or more clinical skills and disposed on the hand portion, the forearm portion, the female external genitalia portion, and the male external genitalia portion.

2. The model of claim 1, wherein the hand portion, the forearm portion, the base portion, the female external genitalia portion, and the male external genitalia portion define a unitary hollow cavity extending therethrough to allow passage of liquid or removable insertion of one or more liquid cartridges proximal to or at the site of the one or more features; and optionally, fingertips of the hand define one or more apertures to drain the liquid externally from the cavity.

3. The model of claim 2, wherein the base portion is frustoconical comprising a circular face, a curved surface, and an edge, and defines an upturned lip disposed on the edge; and optionally, the base portion is removably attached to the forearm portion.

4. The model of claim 1, wherein the stable positions are position is selected from palm upward, index finger and thumb upward, palm downward, or little finger upward.

5. The model of claim 4, wherein the stable position comprises palm upward.

6. The model of claim 5, wherein the hand portion enables simulation of glucose monitoring or splinting.

7. The model of claim 5, wherein the forearm defines a plurality of veins enabling simulation of intravenous insertion and phlebotomy, the veins being selected from a cephalic vein, a median cubital vein, a basilic vein, a pronator vein, a median antebrachial vein, a brachial vein, and paired ulnar veins.

8. The model of claim 4, wherein the stable position comprises index finger and thumb upward.

9. The model of claim 8, wherein the hand portion defines a burn wound enabling simulation of burn management.

10. The model of claim 8, wherein the forearm portion supports a tracheostomy enabling simulation of cleaning and suctioning; and optionally, the forearm supports an ostomy simulating cleaning and removal or attachment of an ostomy pouching system.

11. The model of claim 4, wherein the stable position comprises palm downward.

12. The model of claim 11, wherein the hand portion defines a plurality of veins enabling simulation of intravenous insertion, the veins being selected from a cephalic vein or a dorsal venous network.

13. The model of claim 11, further comprising a wrist portion enabling simulation of casting or splinting.

14. The model of claim 11, wherein the forearm portion defines a simple wound and one or more closing means selected from a staple, suture, skin closure tape, adhesive, or adhesive skin closure to enable simulation of wound management.

15. The model of claim 11, wherein the forearm portion defines a complex wound enabling simulation of wound management.

16. The model of claim 11, wherein the forearm supports one or more draining means selected from a Penrose drain, a Hemovac drain, a Jackson-Pratt drain, or a chest tube drain, to enable simulation of drain management.

17. The model of claim 4, wherein the stable position comprises little finger upward.

18. The model of claim 17, further comprising a nose portion simulating nasogastric intubation in a High Fowler's position.

19. The model of claim 17, wherein the forearm portion supports an ostomy simulating cleaning and removal or attachment of an ostomy pouching system.

20. The model of claim 1, wherein the female external genitalia portion and the male external genitalia portion are configured to simulate urinary catheterization.

* * * * *